(12) United States Patent
Geiger et al.

(10) Patent No.: US 12,728,261 B2
(45) Date of Patent: Sep. 8, 2026

(54) ASSEMBLIES, ELECTRODE LEADS, AND METHODS FOR STEERING AN ELECTRODE LEAD DURING INSERTION INTO A COCHLEA

(71) Applicant: Advanced Bionics LLC, Valencia, CA (US)

(72) Inventors: Stephan Geiger, Hannover (DE); Martin Grossoehmichen, Nienhagen (DE)

(73) Assignee: Advanced Bionics LLC, Valencia, CA (US)

( * ) Notice: Subject to any disclaimer, the term of this patent is extended or adjusted under 35 U.S.C. 154(b) by 263 days.

(21) Appl. No.: 18/381,823

(22) Filed: Oct. 19, 2023

(65) Prior Publication Data

US 2025/0128057 A1 Apr. 24, 2025

(51) Int. Cl.
*A61N 1/05* (2006.01)

(52) U.S. Cl.
CPC .................................. *A61N 1/0541* (2013.01)

(58) Field of Classification Search
CPC .. A61N 1/0541; A61N 1/36036–36038; A61B 17/3468
See application file for complete search history.

(56) References Cited

U.S. PATENT DOCUMENTS 3,760,812 A * 9/1973 Timm ...................... A61N 1/05 607/116
4,215,703 A * 8/1980 Willson .......... A61M 25/09033 604/95.04
5,487,757 A 1/1996 Truckai et al.
6,741,893 B2 * 5/2004 Smits .................. A61N 1/0563 607/122
7,776,062 B2 8/2010 Besselink et al.
7,831,311 B2 * 11/2010 Cross, Jr. ............... A61N 1/056 607/116
7,957,790 B2 6/2011 Kleen
(Continued)

FOREIGN PATENT DOCUMENTS

EP 1189560 B1 3/2006
EP 2539016 A2 1/2013
(Continued)

*Primary Examiner* — Eric D. Bertram
(74) *Attorney, Agent, or Firm* — ALG Intellectual Property, LLC

(57) ABSTRACT

An exemplary assembly may be adapted for insertion into a cochlea. The assembly may comprise a tubular element and an electrode lead having a flexible body and one or more electrode contacts located on the flexible body. The tubular element may comprise a lumen that extends along a length of the flexible body; and a plurality of fiber windings that wrap around and extend along the length of the tubular element. The plurality of fiber windings may include a first section having a first winding configuration and second section having a second winding configuration. In response to application of pressure within the lumen, the first section is configured to move in a first manner based on the first winding configuration and the second section is configured to move in a second manner based on the second winding configuration such that the electrode lead is steerable during insertion into the cochlea.

14 Claims, 10 Drawing Sheets

(56) References Cited

U.S. PATENT DOCUMENTS

| | | | | |
|---|---|---|---|---|
| 8,843,188 | B2 | 9/2014 | Kilgore et al. | |
| 8,843,216 | B2 | 9/2014 | Wallace et al. | |
| 9,211,403 | B2 * | 12/2015 | Tortonese | A61N 1/0541 |
| 9,259,568 | B2 | 2/2016 | Zhao et al. | |
| 9,750,944 | B2 * | 9/2017 | Struve | A61N 1/3718 |
| 10,278,852 | B2 | 5/2019 | Griffin | |
| 11,123,174 | B2 | 9/2021 | Burkart et al. | |
| 11,235,164 | B2 | 2/2022 | Stieghorst et al. | |
| 11,241,557 | B2 * | 2/2022 | Besselink | A61M 25/104 |
| 11,420,045 | B2 | 8/2022 | Sunkeri et al. | |
| 11,464,586 | B2 | 10/2022 | Alvarez et al. | |
| 11,534,078 | B2 | 12/2022 | Tang et al. | |
| 11,554,248 | B1 * | 1/2023 | Tilson | A61M 25/0147 |
| 11,691,003 | B2 * | 7/2023 | Lee | A61N 1/375 607/57 |
| 12,290,679 | B2 * | 5/2025 | Lee | A61N 1/36038 |
| 2002/0049485 | A1 * | 4/2002 | Smits | A61N 1/056 607/122 |
| 2002/0065544 | A1 * | 5/2002 | Smits | A61N 1/0563 607/122 |
| 2006/0089697 | A1 * | 4/2006 | Cross | A61N 1/056 607/122 |
| 2007/0270679 | A1 | 11/2007 | Nguyen et al. | |
| 2012/0277671 | A1 | 11/2012 | Fuentes | |
| 2014/0046250 | A1 * | 2/2014 | Jain | A61M 25/0138 604/95.03 |
| 2015/0343176 | A1 | 12/2015 | Asleson et al. | |
| 2016/0213919 | A1 | 7/2016 | Suwito et al. | |
| 2020/0230361 | A1 * | 7/2020 | Nelson | A61M 25/0043 |
| 2021/0015490 | A1 | 1/2021 | Rangwala et al. | |
| 2021/0322763 | A1 * | 10/2021 | Lee | A61N 1/36038 |
| 2022/0379079 | A1 | 12/2022 | Richter et al. | |
| 2023/0070264 | A1 * | 3/2023 | Leuthardt | A61M 25/0026 |
| 2023/0256239 | A1 * | 8/2023 | Lee | A61N 1/0541 607/57 |

FOREIGN PATENT DOCUMENTS

| | | | |
|---|---|---|---|
| EP | 3510797 | B1 | 6/2020 |
| WO | 2017148903 | A1 | 9/2017 |
| WO | 2022131910 | A1 | 6/2022 |

* cited by examiner

1000

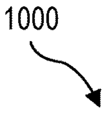

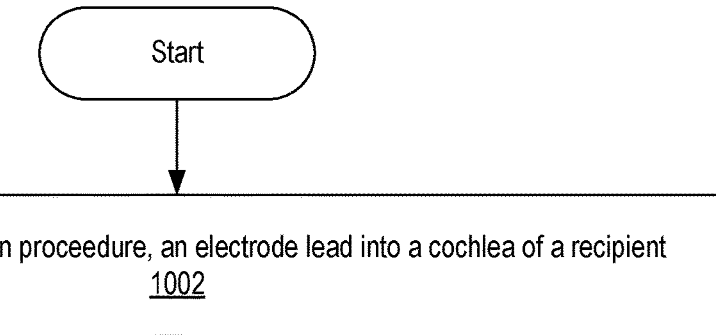

Start

Insert, during a lead insertion proceedure, an electrode lead into a cochlea of a recipient
1002

Steer, during the lead insertion procedure, a distal end of the electrode lead as the electrode lead advances into the cochlea, the steering of the distal end of the electrode lead comprising applying pressure into a lumen of a tubular element that extends along a length of a flexible body of the electrode lead, the tubular element comprising a plurality of fiber windings that wrap around and extend along the length of the tubular element, the plurality of fiber windings including a first section having a first winding configuration and second section having a second winding configuration different from the first winding configuration
1004

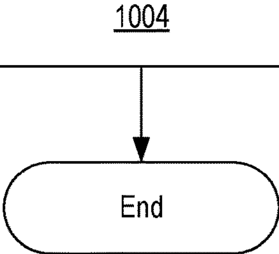

End

Fig. 10

ASSEMBLIES, ELECTRODE LEADS, AND METHODS FOR STEERING AN ELECTRODE LEAD DURING INSERTION INTO A COCHLEA

BACKGROUND INFORMATION

Cochlear implant systems are used to provide, restore, and/or improve the sense of hearing to recipients with severe or profound hearing loss. Conventional cochlear implant systems include various components configured to be implanted within a recipient (e.g., an electronics package, an antenna, and an electrode lead) and various components configured to be located external to the recipient (e.g., a sound processor, a battery, and a microphone).

Correct insertion and placement of an electrode lead within a cochlea for use with a cochlear implant is of great importance for effective electrical stimulation and effective use of the cochlear implant. For example, it is important for the electrode lead to stay within the scala tympani of the cochlea instead of translocating to the scala vestibuli, to be oriented correctly, and to minimize trauma to intracochlear structures so as to preserve any residual hearing that a cochlear implant recipient may have. There are currently multiple tools available (e.g., potential monitoring, imaging, etc.) to investigate and monitor potential trauma, cochlear health status, and electrode lead position before and during insertion of the electrode lead into the cochlea. However, despite such tools a surgeon typically has very limited and indirect control of the movement and position of the electrode lead during insertion. Potential risks associated with such limited control may include incomplete insertion, buckling, tip fold-over, and/or translocation. Accordingly, there remains room to develop electrode leads and methods to provide more control to a surgeon during electrode lead insertion.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 10 shows an exemplary method for steering an electrode lead during insertion into a cochlea according to principles described herein.

DETAILED DESCRIPTION

Assemblies, electrode leads, and methods for steering an electrode lead during insertion into a cochlea are described herein. An exemplary assembly adapted for insertion into a cochlea of a recipient and may comprise a tubular element and an electrode lead having a flexible body and one or more electrode contacts located on the flexible body. The tubular element may comprise a lumen that extends along a length of the flexible body and a plurality of fiber windings that wrap around and extend along the length of the tubular element. The plurality of fiber windings may include a first section having a first winding configuration and second section having a second winding configuration different from the first winding configuration. In response to application of pressure within the lumen, the first section may be configured to move in a first manner based on the first winding configuration and the second section may be configured to move in a second manner based on the second winding configuration such that the electrode lead is steerable during insertion into the cochlea.

The assemblies, electrode leads, and methods described herein may provide various benefits to cochlear implant recipients, as well as others involved with managing cochlear implant systems. For example, assemblies, electrode leads, and methods such as those described herein may facilitate a surgeon efficiently and directly steer an electrode lead during insertion in a manner that prevents or mitigates trauma to intracochlear structures. In addition, assemblies, electrode leads, and methods such as those described herein may facilitate various different movements or combinations of movements that facilitate steering an electrode lead during insertion into a cochlea. For example, electrode leads such as those described herein may be configured to bend, rotate, stretch, etc. in different directions during insertion. As such, multiple movements may be beneficially combined to result in an overall movement and position of an electrode lead with various bending radii, curvatures, directions of movement, etc. Moreover, in certain examples, the steerability of electrode leads such as those described herein may be specific to a side of a recipient's head (e.g., left ear specific or right ear specific) and/or may be individualized or customized to recipient-specific cochlear anatomy.

Various embodiments will now be described in more detail with reference to the figures. The disclosed assemblies, electrode leads, and methods may provide one or more of the benefits mentioned above and/or various additional and/or alternative benefits that will be made apparent herein.

Figure 1:
FIG. 1 illustrates an exemplary cochlear implant system.
Figure 1:
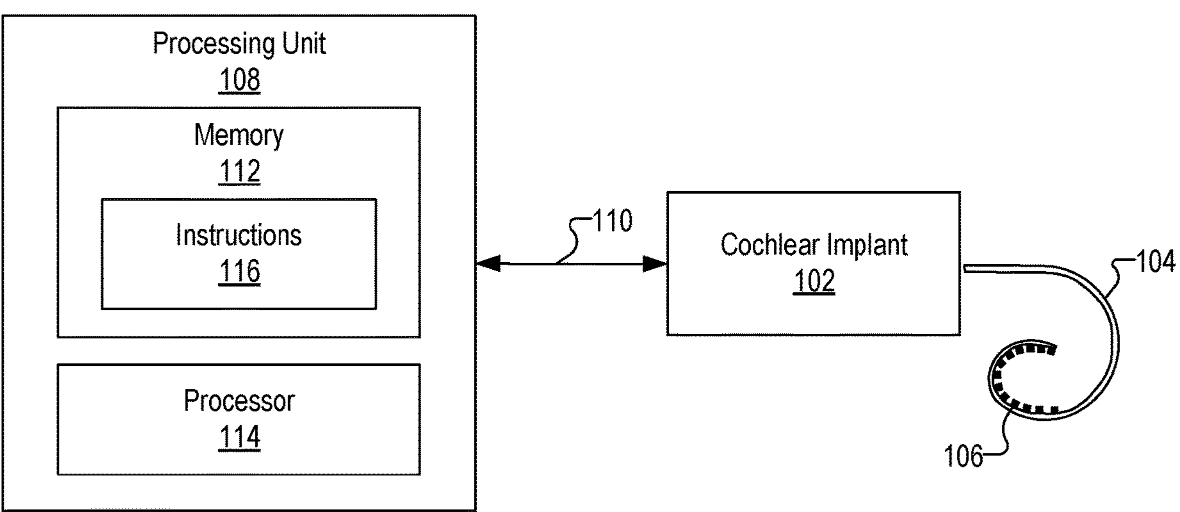

FIG. 1 illustrates an exemplary cochlear implant system 100 configured to be used by a recipient. As shown, cochlear implant system 100 includes a cochlear implant 102, an electrode lead 104 physically coupled to cochlear implant 102 and having an array of electrodes 106, and a processing unit 108 configured to be communicatively coupled to cochlear implant 102 by way of a communication link 110.

The cochlear implant system 100 shown in FIG. 1 is unilateral (i.e., associated with only one ear of the recipient). Alternatively, a bilateral configuration of cochlear implant system 100 may include separate cochlear implants and electrode leads for each ear of the recipient. In the bilateral configuration, processing unit 108 may be implemented by a single processing unit configured to interface with both cochlear implants or by two separate processing units each configured to interface with a different one of the cochlear implants.

Cochlear implant 102 may be implemented by any suitable type of implantable stimulator. For example, cochlear implant 102 may be implemented by an implantable cochlear stimulator. Additionally or alternatively, cochlear implant 102 may be implemented by a brainstem implant and/or any other type of device that may be implanted within the recipient and configured to apply electrical stimulation to one or more stimulation sites located along an auditory pathway of the recipient.

In some examples, cochlear implant 102 may be configured to generate electrical stimulation representative of an audio signal processed by processing unit 108 in accordance with one or more stimulation parameters transmitted to cochlear implant 102 by processing unit 108. Cochlear implant 102 may be further configured to apply the electrical stimulation to one or more stimulation sites (e.g., one or more intracochlear locations) within the recipient by way of one or more electrodes 106 on electrode lead 104. In some examples, cochlear implant 102 may include a plurality of independent current sources each associated with a channel defined by one or more of electrodes 106. In this manner, different stimulation current levels may be applied to multiple stimulation sites simultaneously by way of multiple electrodes 106.

Cochlear implant 102 may additionally or alternatively be configured to generate, store, and/or transmit data. For example, cochlear implant may use one or more electrodes 106 to record one or more signals (e.g., one or more voltages, impedances, evoked responses within the recipient, and/or other measurements) and transmit, by way of communication link 110, data representative of the one or more signals to processing unit 108. In some examples, this data is referred to as back telemetry data.

Electrode lead 104 may be implemented in any suitable manner. For example, a distal portion of electrode lead 104 may be pre-curved such that electrode lead 104 conforms with the helical shape of the cochlea after being implanted. Electrode lead 104 may alternatively be naturally straight or of any other suitable configuration.

In some examples, electrode lead 104 includes a plurality of wires (e.g., within an outer sheath) that conductively couple electrodes 106 to one or more current sources within cochlear implant 102. For example, if there are n electrodes 106 on electrode lead 104 and n current sources within cochlear implant 102, there may be n separate wires within electrode lead 104 that are configured to conductively connect each electrode 106 to a different one of the n current sources. Exemplary values for n are 8, 12, 16, or any other suitable number.

Electrodes 106 are located on at least a distal portion of electrode lead 104. In this configuration, after the distal portion of electrode lead 104 is inserted into the cochlea, electrical stimulation may be applied by way of one or more of electrodes 106 to one or more intracochlear locations. One or more other electrodes (e.g., including a ground electrode, not explicitly shown) may also be disposed on other parts of electrode lead 104 (e.g., on a proximal portion of electrode lead 104) to, for example, provide a current return path for stimulation current applied by electrodes 106 and to remain external to the cochlea after the distal portion of electrode lead 104 is inserted into the cochlea. Additionally or alternatively, a housing of cochlear implant 102 may serve as a ground electrode for stimulation current applied by electrodes 106.

Processing unit 108 may be configured to interface with (e.g., control and/or receive data from) cochlear implant 102. For example, processing unit 108 may transmit commands (e.g., stimulation parameters and/or other types of operating parameters in the form of data words included in a forward telemetry sequence) to cochlear implant 102 by way of communication link 110. Processing unit 108 may additionally or alternatively provide operating power to cochlear implant 102 by transmitting one or more power signals to cochlear implant 102 by way of communication link 110. Processing unit 108 may additionally or alternatively receive data from cochlear implant 102 by way of communication link 110. Communication link 110 may be implemented by any suitable number of wired and/or wireless bidirectional and/or unidirectional links.

As shown, processing unit 108 includes a memory 112 and a processor 114 configured to be selectively and communicatively coupled to one another. In some examples, memory 112 and processor 114 may be distributed between multiple devices and/or multiple locations as may serve a particular implementation.

Memory 112 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 112 may maintain (e.g., store) executable data used by processor 114 to perform one or more of the operations described herein. For example, memory 112 may store instructions 116 that may be executed by processor 114 to perform any of the operations described herein. Instructions 116 may be implemented by any suitable application, program (e.g., sound processing program), software, code, and/or other executable data instance. Memory 112 may also maintain any data received, generated, managed, used, and/or transmitted by processor 114.

Processor 114 may be configured to perform (e.g., execute instructions 116 stored in memory 112 to perform) various operations with respect to cochlear implant 102.

To illustrate, processor 114 may be configured to control an operation of cochlear implant 102. For example, processor 114 may receive an audio signal (e.g., by way of a microphone communicatively coupled to processing unit 108, a wireless interface (e.g., a Bluetooth interface), and/or a wired interface (e.g., an auxiliary input port)). Processor 114 may process the audio signal in accordance with a sound processing program (e.g., a sound processing program stored in memory 112) to generate appropriate stimulation parameters. Processor 114 may then transmit the stimulation parameters to cochlear implant 102 to direct cochlear implant 102 to apply electrical stimulation representative of the audio signal to the recipient.

In some implementations, processor 114 may also be configured to apply acoustic stimulation to the recipient. For example, a receiver (also referred to as a loudspeaker) may be optionally coupled to processing unit 108. In this configuration, processor 114 may deliver acoustic stimulation to the recipient by way of the receiver. The acoustic stimulation may be representative of an audio signal (e.g., an amplified version of the audio signal), configured to elicit an evoked response within the recipient, and/or otherwise configured. In configurations in which processor 114 is configured to both deliver acoustic stimulation to the recipient and direct cochlear implant 102 to apply electrical stimulation to the recipient, cochlear implant system 100 may be referred to as a bimodal hearing system and/or any other suitable term.

Processor 114 may be additionally or alternatively configured to receive and process data generated by cochlear implant 102. For example, processor 114 may receive data representative of a signal recorded by cochlear implant 102 using one or more electrodes 106 and, based on the data, adjust one or more operating parameters of processing unit 108. Additionally or alternatively, processor 114 may use the data to perform one or more diagnostic operations with respect to cochlear implant 102 and/or the recipient.

Other operations may be performed by processor 114 as may serve a particular implementation. In the description provided herein, any references to operations performed by processing unit 108 and/or any implementation thereof may be understood to be performed by processor 114 based on instructions 116 stored in memory 112.

Figure 2:
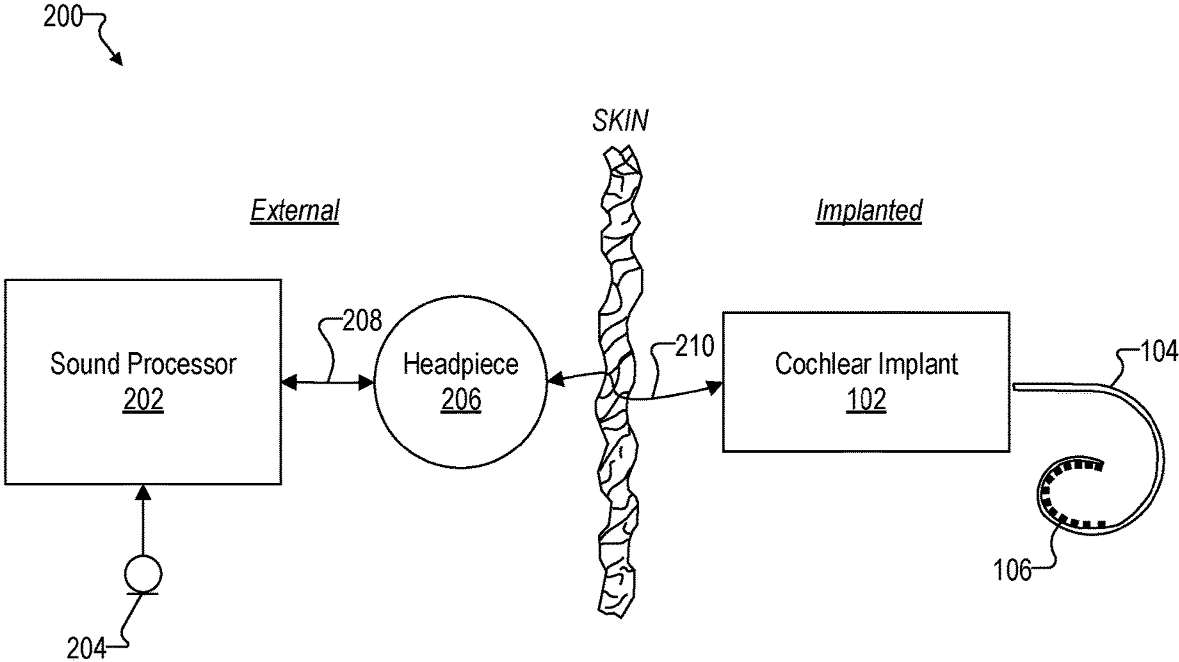
FIG. 2 shows an exemplary configuration of the cochlear implant system of FIG. 1.

Processing unit 108 may be implemented by one or more devices configured to interface with cochlear implant 102. To illustrate, FIG. 2 shows an exemplary configuration 200 of cochlear implant system 100 in which processing unit 108 is implemented by a sound processor 202 configured to be located external to the recipient. In configuration 200, sound processor 202 is communicatively coupled to a microphone 204 and to a headpiece 206 that are both configured to be located external to the recipient.

Sound processor 202 may be implemented by any suitable device that may be worn or carried by the recipient. For example, sound processor 202 may be implemented by a behind-the-ear ("BTE") unit configured to be worn behind and/or on top of an ear of the recipient. Additionally or alternatively, sound processor 202 may be implemented by an off-the-ear unit (also referred to as a body worn device) configured to be worn or carried by the recipient away from the ear. Additionally or alternatively, at least a portion of sound processor 202 is implemented by circuitry within headpiece 206.

Microphone 204 is configured to detect one or more audio signals (e.g., that include speech and/or any other type of sound) in an environment of the recipient. Microphone 204 may be implemented in any suitable manner. For example, microphone 204 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 202. Additionally or alternatively, microphone 204 may be implemented by one or more microphones in or on headpiece 206, one or more microphones in or on a housing of sound processor 202, one or more beam-forming microphones, and/or any other suitable microphone as may serve a particular implementation.

Headpiece 206 may be selectively and communicatively coupled to sound processor 202 by way of a communication link 208 (e.g., a cable or any other suitable wired or wireless communication link), which may be implemented in any suitable manner. Headpiece 206 may include an external antenna (e.g., a coil and/or one or more wireless communication components) configured to facilitate selective wireless coupling of sound processor 202 to cochlear implant 102. Headpiece 206 may additionally or alternatively be used to selectively and wirelessly couple any other external device to cochlear implant 102. To this end, headpiece 206 may be configured to be affixed to the recipient's head and positioned such that the external antenna housed within headpiece 206 is communicatively coupled to a corresponding implantable antenna (which may also be implemented by a coil and/or one or more wireless communication components) included within or otherwise connected to cochlear implant 102. In this manner, stimulation parameters and/or power signals may be wirelessly and transcutaneously transmitted between sound processor 202 and cochlear implant 102 by way of a wireless communication link 210.

In configuration 200, sound processor 202 may receive an audio signal detected by microphone 204 by receiving a signal (e.g., an electrical signal) representative of the audio signal from microphone 204. Sound processor 202 may additionally or alternatively receive the audio signal by way of any other suitable interface as described herein. Sound processor 202 may process the audio signal in any of the ways described herein and transmit, by way of headpiece 206, stimulation parameters to cochlear implant 102 to direct cochlear implant 102 to apply electrical stimulation representative of the audio signal to the recipient.

In an alternative configuration, sound processor 202 may be implanted within the recipient instead of being located external to the recipient. In this alternative configuration, which may be referred to as a fully implantable configuration of cochlear implant system 100, sound processor 202 and cochlear implant 102 may be combined into a single device or implemented as separate devices configured to communicate one with another by way of a wired and/or wireless communication link. In a fully implantable implementation of cochlear implant system 100, headpiece 206 may not be included and microphone 204 may be implemented by one or more microphones implanted within the recipient, located within an ear canal of the recipient, and/or external to the recipient.

Figure 3:
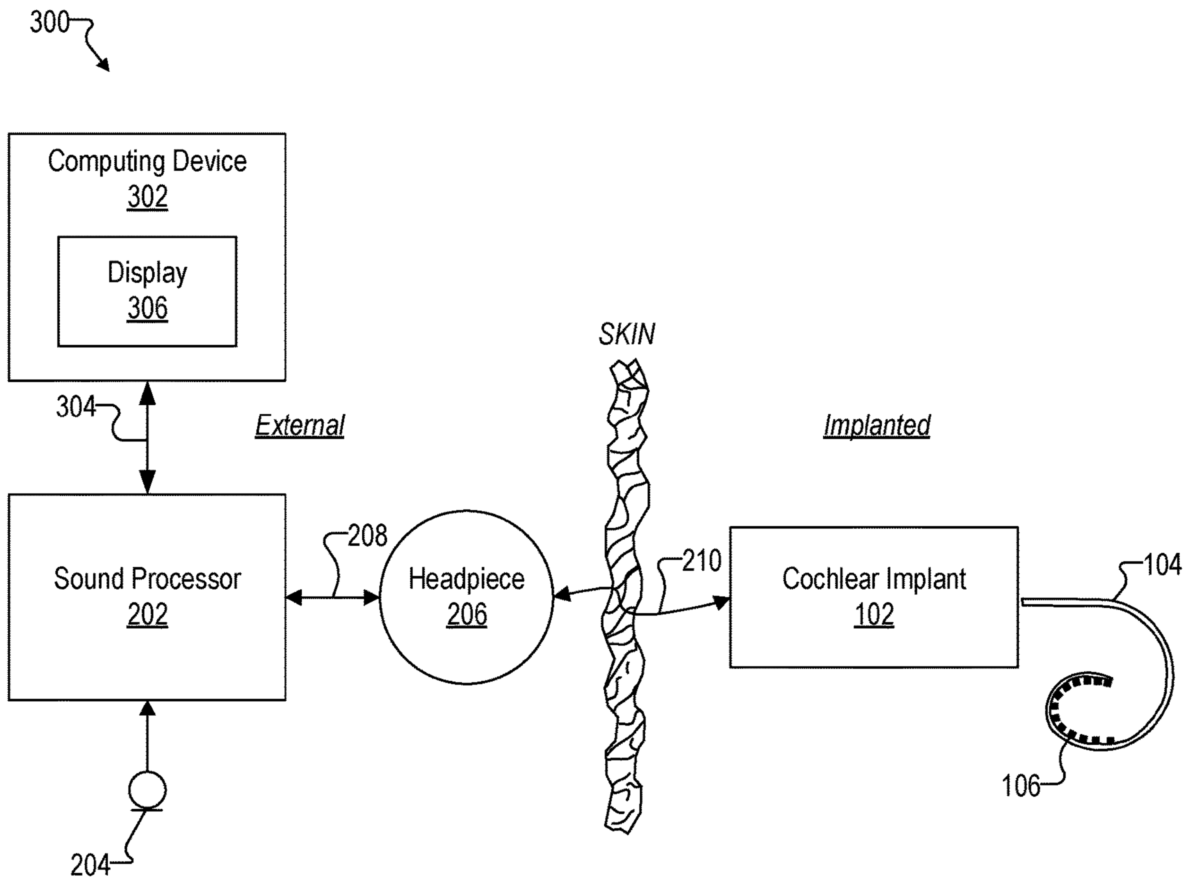
FIG. 3 shows another exemplary configuration of the cochlear implant system of FIG. 1.

FIG. 3 shows an exemplary configuration 300 of cochlear implant system 100 in which processing unit 108 is implemented by a combination of sound processor 202 and a computing device 302 configured to communicatively couple to sound processor 202 by way of a communication link 304, which may be implemented by any suitable wired or wireless communication link.

Computing device 302 may be implemented by any suitable combination of hardware and software. To illustrate, computing device 302 may be implemented by a mobile device (e.g., a mobile phone, a laptop, a tablet computer, etc.), a desktop computer, and/or any other suitable computing device as may serve a particular implementation. As an example, computing device 302 may be implemented by a mobile device configured to execute an application (e.g., a "mobile app") that may be used by a user (e.g., the recipient, a clinician, and/or any other user) to control one or more settings of sound processor 202 and/or cochlear implant 102 and/or perform one or more operations (e.g., diagnostic operations) with respect to data generated by sound processor 202 and/or cochlear implant 102.

In some examples, computing device 302 may be configured to control an operation of cochlear implant 102 by transmitting one or more commands to cochlear implant 102 by way of sound processor 202. Likewise, computing device 302 may be configured to receive data generated by cochlear implant 102 by way of sound processor 202. Alternatively, computing device 302 may interface with (e.g., control and/or receive data from) cochlear implant 102 directly by way of a wireless communication link between computing device 302 and cochlear implant 102. In some implementations in which computing device 302 interfaces directly with cochlear implant 102, sound processor 202 may or may not be included in cochlear implant system 100.

Computing device 302 is shown as having an integrated display 306. Display 306 may be implemented by a display screen, for example, and may be configured to display content generated by computing device 302. Additionally or alternatively, computing device 302 may be communicatively coupled to an external display device (not shown) configured to display the content generated by computing device 302.

In some examples, computing device 302 may represent any suitable device that may facilitate insertion of an electrode lead such as electrode lead 104 into a cochlea. In such examples, computing device 302 may be configured in any suitable manner. For example, computing device 302 may be configured in any suitable manner to measure an evoked response elicited within a recipient of the cochlear implant by stimulation (e.g., electrical stimulation and/or acoustic stimulation). Such evoked responses may be used in any suitable manner to determine whether a translocation event is about to occur or has occurred. Additionally or alternatively, computing device 302 may be configured to capture any suitable images of a recipient during insertion to facilitate a surgeon visualizing the cochlea and steering an electrode lead (e.g., electrode lead 104) during insertion in any suitable manner such as described herein. Additionally or alternatively, computing device 302 may provide a three-dimensional model of the cochlea for display to a surgeon during an insertion procedure to facilitate the surgeon steering an electrode lead.

In some examples, computing device 302 represents a fitting device configured to be selectively used (e.g., by a clinician) to fit sound processor 202 and/or cochlear implant 102 to the recipient. In these examples, computing device 302 may be configured to execute a fitting program configured to set one or more operating parameters of sound processor 202 and/or cochlear implant 102 to values that are optimized for the recipient. As such, in these examples, computing device 302 may not be considered to be part of cochlear implant system 100. Instead, computing device 302 may be considered to be separate from cochlear implant system 100 such that computing device 302 may be selectively coupled to cochlear implant system 100 when it is desired to fit sound processor 202 and/or cochlear implant 102 to the recipient.

Figure 4:
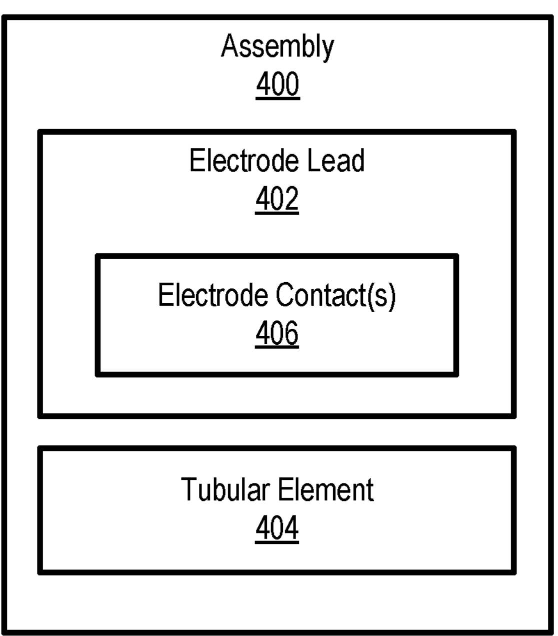
FIG. 4 shows an assembly that may be implemented according to principles described herein.

There are various potential risks associated with inserting an electrode lead (e.g., electrode lead 104) into a cochlea. For example, there may be incomplete insertion, buckling, a tip fold-over, and/or a scalar translocation. Assemblies, electrode leads, and methods such as those described herein are configured such that an electrode lead is steerable during insertion into the cochlea to mitigate such risks. FIG. 4 illustrates an exemplary assembly 400 that may be implemented according to principles described herein. As shown, assembly 400 may include, without limitation, an electrode lead 402 and a tubular element 404. Electrode lead 402 may be configured in any suitable manner such as described herein. For example, electrode lead 402 may have a flexible body (e.g., formed of silicone) and one or more electrode contacts 406 located on (e.g., an outer surface) of the flexible body. In certain examples, electrode lead 402 may correspond to a straight electrode lead. In certain alternative examples, electrode lead 402 may correspond to a pre-curved electrode lead.

Tubular element 404 may be formed of any suitable material as may serve a particular implementation. For example, tubular element 404 may be formed of silicone in certain examples. Tubular element 404 may be configured in any suitable manner. For example, tubular element 404 may comprise a lumen that extends along a length of the flexible body of electrode lead 402. In addition, tubular element 404 may comprise a plurality of fiber windings that wrap around and extend along a length of tubular element 404. The plurality of fiber windings may be formed of any suitable fiber material as may serve a particular implementation. For example, the plurality of fiber windings may be formed of carbon fibers, glass fibers, polymer fibers, and/or any other suitable type of fiber in any suitable combination.

Sections of the fiber windings of tubular element 404 may be configured to move in a specific manner in response to applied pressure depending on the configuration of the fiber windings in those sections. The fiber windings may have any suitable number and/or combinations of sections as may serve a particular implementation. For example, the plurality of fiber windings may include a first section having a first winding configuration and a second section having a second winding configuration different than the first winding configuration. In certain examples, the plurality of fiber windings may further include a third section having a third winding configuration. In certain examples, the third winding configuration may be different than the first winding configuration and the second winding configuration. In certain alternative examples, the third winding configuration may be the same winding configuration as either the first winding configuration or the second winding configuration.

Electrode lead 402 is configured such that pressure applied within the lumen of tubular element 404 causes electrode lead 402 to move in a particular manner depending on the configuration of the fiber windings along the length of tubular element 404. For example, in response application of pressure within the lumen, the first section may be configured to move in a first manner based on the first winding configuration and the second section may be configured to move in a second manner based on the second winding configuration such that electrode lead 402 is steerable during insertion into the cochlea. In examples, the third section may be configured to move in a third manner based on the third winding configuration.

The first section and the second section may move in any suitable manner depending on the fiber winding configuration within each section. For example, the first section may be configured to move in the first manner based on the first winding configuration by extending, expanding, twisting, or bending. The second section may be configured to move in the second manner based on the first winding configuration by extending, expanding, twisting, or bending. In certain examples, the first section and the second section may be configured to have the same type of movement in response to pressure within the lumen. For example, the first section and the second section may each be configured to have a bending movement in response to pressure applied within the lumen. In such examples, the first section may bend in the same direction as the second section but to a greater degree than the second section. Alternatively, the first section may bend in a first direction and the second section may bend in a second direction different than the first direction. In certain alternative implementations, the first section and the second section may each have a different type of movement. For example, the first section may be configured to twist and the second section may be configured to bend in response to the application of pressure.

In certain examples, the first manner of movement of the first section and the third manner of movement of the third section may each be associated with the same type of movement. For example, the first manner of movement and the third manner of movement may both correspond to bending movements.

In certain examples, the amount that a section of a tubular element moves may be proportional to the amount of pressure applied into the lumen. For example, an amount that the first section moves in the first manner and an amount that the second section moves in the second manner may increase in proportion to an amount of pressure applied into the lumen. In so doing, it may be possible to increase or decrease the amount of pressure applied into the lumen during insertion to steer the electrode lead.

In certain examples, the amount of pressure applied within a lumen of a tubular element may result in different sections moving by different amounts even though they are associated with the same type of movement. For example, in response to the application of pressure within the lumen, the first section may be configured to move by a first amount and the third section may configured to move by a second amount that is greater than the first amount.

Any suitable type of pressure may be applied within the lumen of tubular element 404 as may serve a particular implementation. For example, in certain implementations gas pressure may be applied in any suitable manner into the lumen. In certain alternative implementations, liquid pressure may be applied in any suitable manner into the lumen. The pressure may be applied within the lumen in any suitable manner. For example, a syringe may be attached to an inlet of the lumen. A position of a plunger of the syringe may be varied to either increase or decrease the amount of pressure within the lumen.

Figure 5:
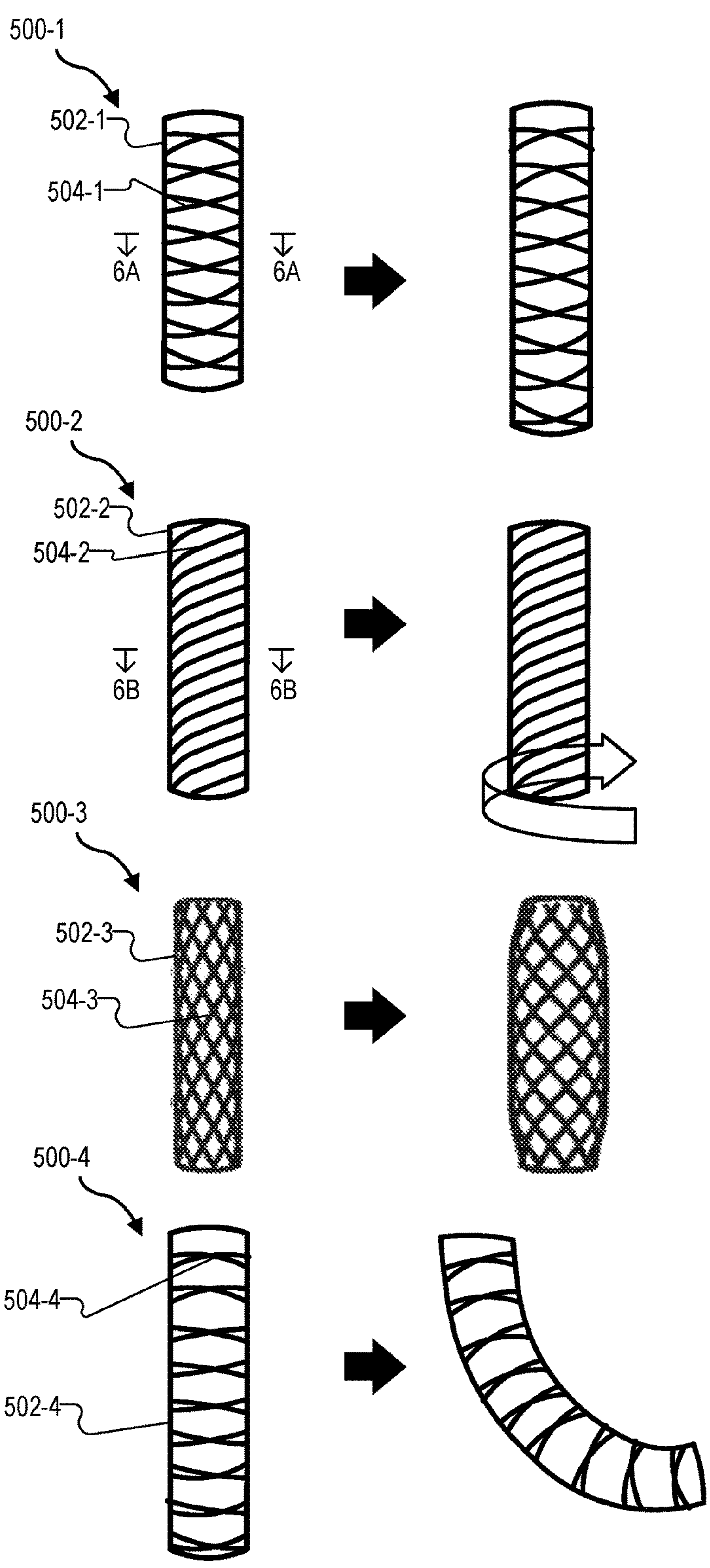
FIG. 5 shows exemplary configurations of windings that may be implemented according to principles described herein for different types of movement.

FIG. 5 illustrates various different sections 500 (e.g., sections 500-1 through 500-4) that may be implemented in tubular element 404 according to principles described herein. As shown in FIG. 5, each section 500 has a wall portion 502 (e.g., wall portions 502-1 through 502-4) and a different configuration of fiber windings 504 (e.g., fiber windings 504-1 through 504-4). Sections 500 represent different possible sections of fiber windings that may be implemented along a length of tubular element 404 to cause different movements at portions of electrode lead 402 during insertion. For example, the configuration of fiber windings 504-1 may cause section 500-1 to extend as shown in FIG. 5 in response to the application of pressure within the lumen. The configuration of fiber windings 504-2 may cause section 500-2 to rotate as shown in FIG. 5 in response to the application of pressure within the lumen. The configuration of fiber windings 504-3 may cause section 500-3 to expand as shown in FIG. 5 in response to the application of pressure within the lumen. The configuration of fiber windings 504-4 may cause section 500-4 to bend as shown in FIG. 5 in response to the application of pressure within the lumen. The exemplary sections shown in FIG. 5 are provided for illustrative purposes only. It is understood that any suitable number of different sections and/or configurations of fiber windings may be used in different implementations.

Figure 6A:
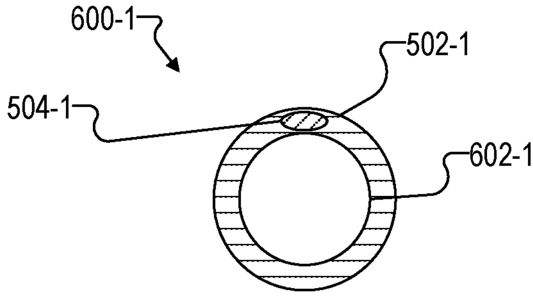
FIG. 6A is an exemplary enlarged cross section taken along lines 6A-6A in FIG. 5 according to principles described herein.

Fiber windings such as fiber windings 504 may extend along a length of tubular element 404 in any suitable manner. For example, in certain implementations, a plurality of fiber windings may be embedded within a wall of tubular element 404. To illustrate, FIG. 6A shows an exemplary cross section 600-1 of section 500-1 taken along lines 6A-6A in FIG. 5. As shown in FIG. 6A, wall portion 502-1 defines a lumen 602-1 within section 500-1. In the example shown in FIG. 6A, fiber winding 504-1 is completely embedded within wall portion 502-1 such that the material forming wall portion 502-1 completely surrounds fiber winding 504-1. In certain alternative implementations, fiber winding 504-1 may be partially embedded within wall portion 502-1.

Figure 6B:
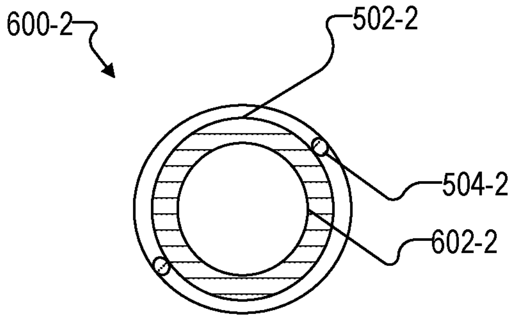
FIG. 6B is an exemplary enlarged cross section taken along lines 6B-6B in FIG. 5 according to principles described herein.

In certain alternative implementations, a plurality of fiber windings may be wrapped around an outer surface of tubular element 404 instead of being embedded within tubular element 404. To illustrate, FIG. 6B shows an exemplary cross section 600-2 of section 500-2 taken along lines 6B-6B in FIG. 5. As shown in FIG. 6B, wall portion 502-2 defines a lumen 602-2 within section 500-2. In the example shown in FIG. 6B, fiber winding 504-2 wraps around an outer surface or wall portion 502-2.

FIGS. 6A and 6B show wall portions 502-1 and 502-2 as having a circular cross-sectional shape. However, it is understood that the wall portion of a tubular element may have any other suitable cross-sectional shape (e.g., oval, square, etc.) as may serve a particular implementation.

In certain alternative implementations, the same section of tubular element 404 may have some fiber windings embedded within a wall of tubular element 404 and some fiber windings that wrap around an outer surface of tubular element 404.

Figure 7:
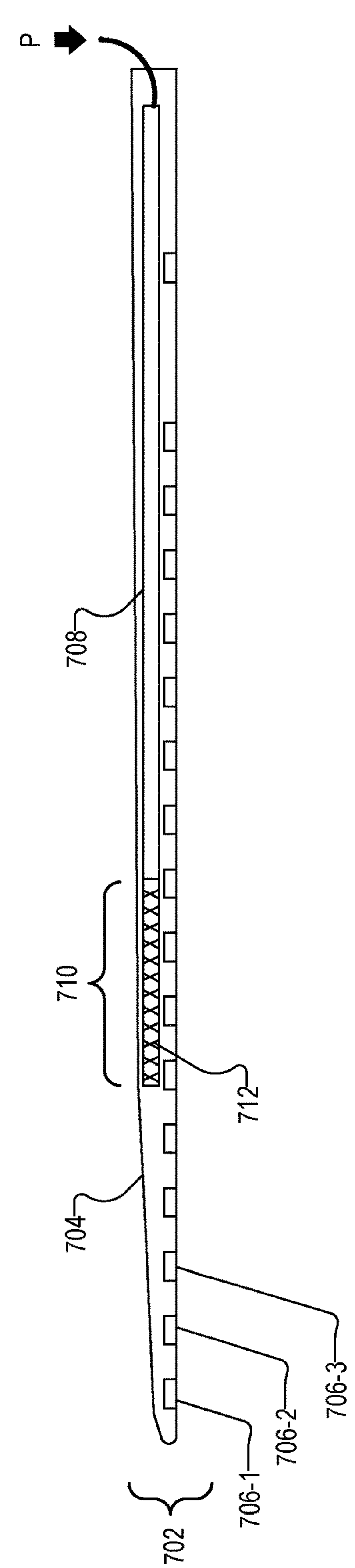
FIGS. 7-9 are exemplary configurations of the assembly of FIG. 4 according to principles described herein.

Tubular element 404 may be provided together with electrode lead 402 in any suitable manner. For example, in certain implementations, tubular element 404 may be embedded within the flexible body of electrode lead 402. To illustrate, FIG. 7 shows an exemplary configuration 700 that assembly 400 may have in certain implementations. As shown in FIG. 7, configuration 700 includes an electrode lead 702 that includes a flexible body 704 and a plurality of electrode contacts 706 (e.g., electrode contacts 706-1 through 706-3). In the example shown in FIG. 7, a tubular element 708 is embedded within flexible body 704 and extends along a length of flexible body 704. Tubular element 708 includes a section 710 having fiber windings 712. Section 710 is configured to move in any suitable manner, such as described herein, upon application of pressure into a lumen of tubular element 708. For example, based on the winding configuration of fiber windings 712, section 710 may be configured to bend downward during insertion when pressure is applied into the lumen. In certain examples, tubular element 404 may be embedded within electrode lead 402 by being inserted within a stylet lumen of electrode lead 402.

Figure 8:
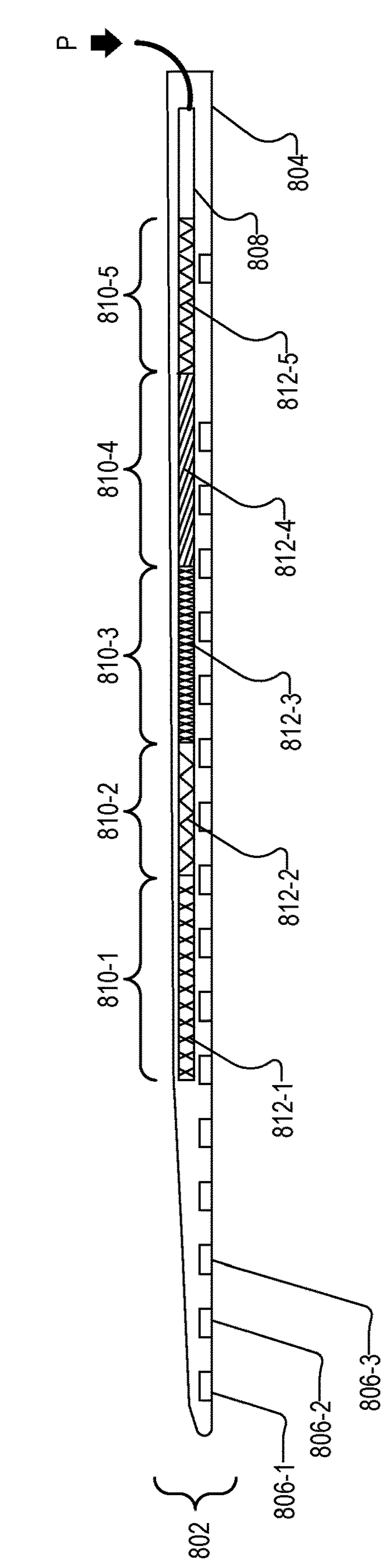

In the example shown in FIG. 7, tubular element 708 only has one section 710 with fiber windings 712. Certain alternative implementations may include a plurality of different sections with the same or different fiber winding configurations. To illustrate, FIG. 8 shows an exemplary configuration 800 of assembly 400 where a tubular element includes a plurality of different sections with different fiber windings. As shown in FIG. 8, configuration 800 includes an electrode lead 802 that includes a flexible body 804 and a plurality of electrode contacts 806 (e.g., electrode contacts 806-1 through 806-3). In the example shown in FIG. 8, a tubular element 808 is embedded within flexible body 804 and extends along a length of flexible body 804. In the implementation shown in FIG. 8, tubular element 808 includes a plurality of sections 810 (e.g., sections 810-1 through 810-5) provided along a length of flexible body 804. Each section 810 includes fiber windings 812 that are configured to cause a portion of electrode lead 802 to move in a particular manner upon application of pressure into a lumen of tubular element 808. Sections 810 may be configured to move in any suitable manner, such as described herein. For example, based on the winding configuration of fiber windings 812-1, section 810-1 may bend downward in response to pressure being applied into the lumen. Based on the winding configuration of fiber windings 812-2, section 810-2 may twist in response to pressure being applied into the lumen. Based on the winding configuration of fiber windings 812-3, section 810-3 may bend to the left in response to pressure being applied into the lumen, and so forth.

In certain examples, a tubular element may be provided along an outer surface of a flexible body of an electrode lead. In such examples, the tubular element may be detachable from the electrode lead and may be configured to be removed from the electrode lead upon insertion of the electrode lead into the cochlea. In such examples, the tubular element may be detachable from the electrode lead in any suitable manner. For example, one or more fastening elements (e.g., clips, lashes, etc.) may be provided along a length of the tubular element to secure the tubular element to the electrode lead during insertion. After insertion is completed, the one or more fastening elements may be released in any suitable manner and the tubular element may be withdrawn from the recipient.

Figure 9:
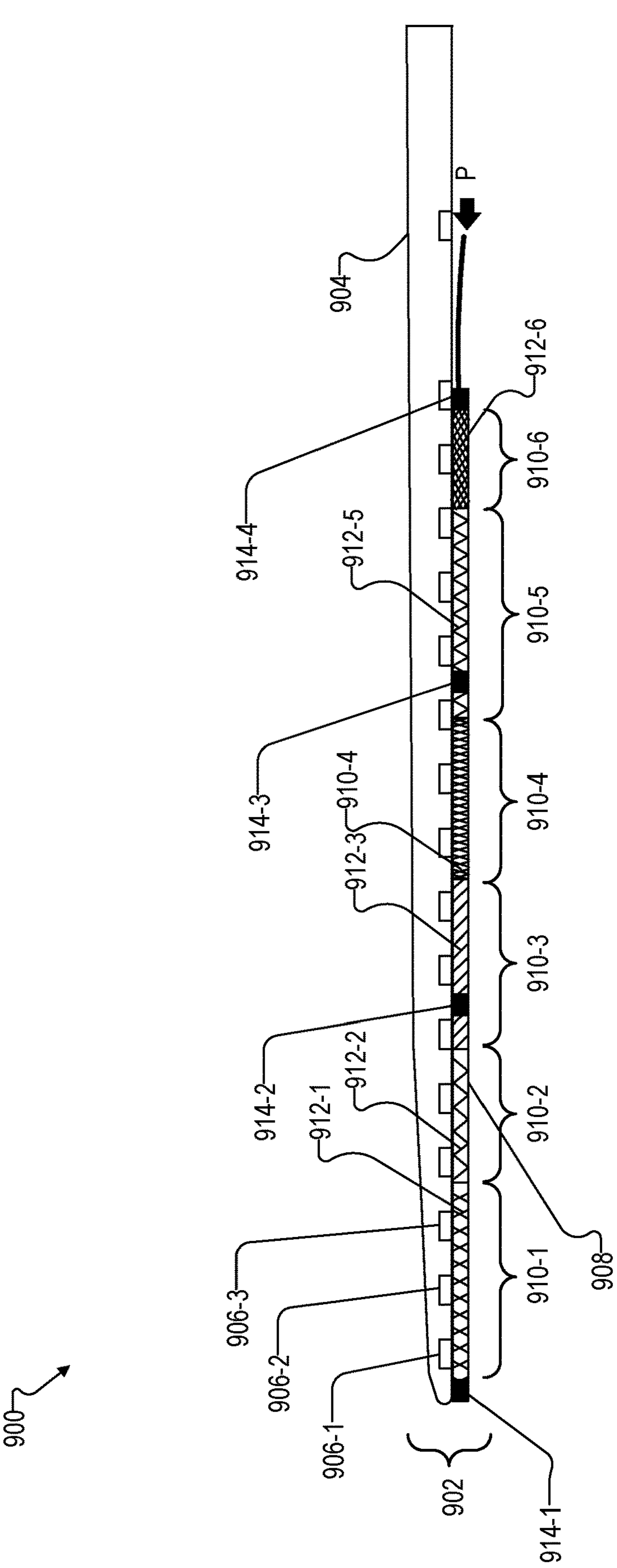

FIG. 9 illustrates an exemplary configuration 900 of assembly 400 where a tubular element is provided along an outer surface of a flexible body. As shown in FIG. 9, configuration 900 includes an electrode lead 902 that includes a flexible body 904 and a plurality of electrode contacts 906 (e.g., electrode contacts 906-1 through 906-3). In the example shown in FIG. 9, a tubular element 908 is provided along a lower outer surface of flexible body 904. Tubular element 908 includes a plurality of sections 910 (e.g., section 910-1 through 910-6). Each of sections 910 has fiber windings 912 (e.g., fiber windings 912-1 through 912-6). Sections 910 are configured to move in any suitable manner, such as described herein, upon application of pressure into a lumen of tubular element 908. In the example shown in FIG. 9, a plurality of fastening elements 914 (e.g., fastening elements 914-1 through 914-4) are provided to secure tubular element 908 to the outer surface of flexible body 904 during insertion into the cochlea. After electrode lead 902 is inserted within the cochlea, fastening elements 914 may release from flexible body 904 such that tubular element 908 may be removed from electrode lead 902.

FIGS. 7-9 show only one tubular element provided together with each electrode lead. However, it is understood that alternative implementations may include electrode leads that have two or more tubular elements that extend along the length of the electrode lead. Each of the two or more tubular elements may include one or more sections with fiber windings such as those described herein. For example, an electrode lead may include a first tubular element embedded within a flexible body of an electrode lead and a second tubular element embedded within the flexible body. Alternatively, an electrode lead may include a first tubular element that is embedded within a flexible body of the electrode lead and a second tubular element that is provided along an outer surface of the electrode lead. With such configurations it may be possible to provide more combinations of movements and/or individually control different movements to steer the electrode lead during insertion into the cochlea.

In certain examples, a cross sectional wall thickness of one or more sections of a tubular element may be varied to facilitate steering an electrode lead during insertion into the cochlea. For example, a tubular element may have a first wall thickness at a first section and a second wall thickness at a second section. The first wall thickness may be greater than the second wall thickness. In such examples, in response to the application of pressure within the lumen, the second section may be configured to move in the second manner prior to the first section moving in the first manner.

In certain examples, tubular elements such as those described herein may be side specific. In such examples, the tubular element may be configured to be inserted within a cochlea positioned on a specific side of a head of a recipient. For example, the one or more sections of the tubular element may include different sections of fiber windings that cause the electrode lead to bend, curve, etc. in an manner that is specific to the cochlea on the left side of the head of the recipient.

In certain examples, a tubular element may be custom formed for a recipient based on individual cochlea geometry of the cochlea of the recipient. Such a custom formed tubular element may be formed in any suitable manner. For example, a custom three-dimensional model of the cochlea for a specific recipient may be used in any suitable manner to determine the movement or combinations of movements that would be helpful to facilitate steering an electrode lead during insertion within the specific recipient.

In certain examples, a tubular element such as described herein may be inserted into a lumen of a flexible body. For example, the tubular element may be inserted within a stylet lumen of the flexible body. In such examples, the tubular element may be configured to be removed from the lumen of the flexible body upon insertion of the electrode lead into the cochlea.

Although the preceding description is described in the context of a cochlear implant system, it is understood that concepts such as those described herein may be applied in other contexts with other types of implantable electrode leads.

FIG. 10 illustrates an exemplary method 1000 for steering an electrode lead during insertion into a cochlea. While FIG. 10 illustrates exemplary operations according to one embodiment, other embodiments may omit, add to, reorder, and/or modify any of the operations shown in FIG. 10.

At operation 1002, an electrode lead may be inserted into a cochlea of a recipient during a lead insertion procedure. Operation 1002 may be performed in any of the ways described herein.

At operation 1004, the hearing care professional (e.g., surgeon) may steer, during the lead insertion procedure, a distal end of the electrode lead as the electrode lead advances into the cochlea. The steering of the distal end of the electrode lead may comprise applying pressure into a lumen of a tubular element that extends along a length of a flexible body of the electrode lead. The tubular element may comprise a plurality of fiber windings that wrap around and extend along a length of the tubular element. The plurality of fiber windings may include a first section having a first winding configuration and a second section having a second winding configuration different from the first winding configuration. In response to the application of pressure within the lumen, the first section may move in a first manner based on the first winding configuration and the second section may move in a second manner based on the second winding configuration. Operation 1004 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An assembly adapted for insertion into a cochlea of a recipient, the assembly comprising:

an electrode lead having a flexible body and one or more electrode contacts located on the flexible body; and a tubular element comprising:

a lumen that extends along a length of the flexible body; and a plurality of fiber windings that wrap around and extend along a length of the tubular element, the plurality of fiber windings including a first section having a first winding configuration and second section having a second winding configuration different from the first winding configuration, wherein:

in response to application of pressure within the lumen, the first section is configured to move in a first manner based on the first winding configuration and the second section is configured to move in a second manner based on the second winding configuration such that the electrode lead is steerable during insertion into the cochlea;

the tubular element is inserted into a lumen of the flexible body; and the tubular element is configured to be removed from the lumen of the flexible body upon insertion of the electrode lead into the cochlea.

2. The assembly of claim 1, wherein the plurality of fiber windings are embedded within a wall of the tubular element.

3. The assembly of claim 1, wherein the plurality of fiber windings are wrapped around an outer surface of the tubular element.

4. The assembly of claim 1, wherein:

the first section is configured to move in the first manner based on the first winding configuration by extending, expanding, twisting, or bending; and the second section is configured to move in the second manner based on the second winding configuration by extending, expanding, twisting, or bending.

5. The assembly of claim 1, wherein:

the plurality of fiber windings further includes a third section having a third winding configuration; and the third section is configured to move in a third manner based on the third winding configuration.

6. The assembly of claim 5, wherein the third winding configuration is different than the first winding configuration and the second winding configuration.

7. The assembly of claim 5, wherein:

the first manner of movement of the first section and the third manner of movement of the third section are each associated with the same type of movement; and in response to the application of pressure within the lumen of the tubular element, the first section is configured to move by a first amount and the third section is configured to move by a second amount that is greater than the first amount.

8. The assembly of claim 1, wherein:

the tubular element has a first wall thickness at the first section and a second wall thickness at the second section;

the first wall thickness is greater than the second wall thickness; and in response to the application of the pressure within the lumen of the tubular element, the second section is configured to move in the second manner prior to the first section moving in the first manner.

9. The assembly of claim 1, wherein the pressure is applied by way of gas pressure being applied into the lumen of the tubular element or by way of liquid pressure being applied into the lumen of the tubular element.

10. The assembly of claim 1, wherein the tubular element is side specific and is configured to be inserted within the cochlea positioned on a specific side of a head of the recipient.

11. The assembly of claim 1, wherein the tubular element is custom formed for the recipient based on individual cochlea geometry of the cochlea of the recipient.

12. An electrode lead comprising:

a flexible body;

one or more electrode contacts located on the flexible body; and a tubular element embedded within the flexible body, the tubular element comprising:

a lumen that extends along a length of the flexible body; and a plurality of fiber windings that wrap around and extend along a length of the tubular element, the plurality of fiber windings including a first section having a first winding configuration and second section having a second winding configuration different from the first winding configuration, wherein, in response to application of pressure within the lumen, the first section is configured to move in a first manner based on the first winding configuration and the second section is configured to move in a second manner based on the second winding configuration such that the electrode lead is steerable during insertion into a cochlea of a recipient.

13. The electrode lead of claim 12, wherein:

the first section is configured to move in the first manner based on the first winding configuration by extending, expanding, twisting, or bending; and the second section is configured to move in the second manner based on the second winding configuration by extending, expanding, twisting, or bending.

14. An assembly adapted for insertion into a cochlea of a recipient, the assembly comprising:

an electrode lead having a flexible body and one or more electrode contacts located on the flexible body; and a tubular element comprising:

a lumen that extends along a length of the flexible body; and a plurality of fiber windings that wrap around and extend along a length of the tubular element, the plurality of fiber windings including a first section having a first winding configuration and second section having a second winding configuration different from the first winding configuration, wherein:

in response to application of pressure within the lumen, the first section is configured to move in a first manner based on the first winding configuration and the second section is configured to move in a second manner based on the second winding configuration such that the electrode lead is steerable during insertion into the cochlea; and the tubular element is embedded within the flexible body.

* * * * *